US006924114B2

(12) United States Patent
Wyant et al.

(10) Patent No.: US 6,924,114 B2
(45) Date of Patent: Aug. 2, 2005

(54) METHOD FOR MONITORING RESTING AND ACTIVATED PLATELETS IN UNFIXED BLOOD SAMPLES

(75) Inventors: Timothy L. Wyant, Fremont, CA (US); Paul A. Raju, Union City, CA (US); Aaron B. Kantor, San Carlos, CA (US)

(73) Assignee: SurroMed, Inc., Menlo Park, CA (US)

( * ) Notice: Subject to any disclaimer, the term of this patent is extended or adjusted under 35 U.S.C. 154(b) by 310 days.

(21) Appl. No.: 09/957,624

(22) Filed: Sep. 20, 2001

(65) Prior Publication Data

US 2002/0160523 A1 Oct. 31, 2002

Related U.S. Application Data

(60) Provisional application No. 60/234,065, filed on Sep. 20, 2000.

(51) Int. Cl.[7] .............................. G01N 33/53; G01N 1/00
(52) U.S. Cl. .............................. 435/7.2; 435/2; 435/7.1; 435/7.2; 435/7.21; 435/374; 435/375; 436/517; 436/546; 436/18; 436/63; 436/69; 436/164; 436/166; 436/171; 436/172; 436/173; 436/176
(58) Field of Search .......................... 435/7.1, 7.2, 7.21, 435/7.8, 7.92, 362, 374, 375, 2; 436/516, 517, 546, 63, 69, 164, 171, 172, 173, 176, 800, 166, 18; 514/170

(56) References Cited

U.S. PATENT DOCUMENTS

| | | | |
|---|---|---|---|
| 5,529,902 A | | 6/1996 | Kottke et al. |
| 5,547,849 A | | 8/1996 | Baer et al. |
| 5,556,764 A | | 9/1996 | Sizto et al. |
| 6,230,713 B1 | * | 5/2001 | Dalesandro et al. ........ 128/898 |

FOREIGN PATENT DOCUMENTS

| | | |
|---|---|---|
| EP | 0 984 280 A1 | 3/1999 |
| FR | 002729823 A1 | 1/1995 |
| US | WO 01/08081 | 2/2001 |

OTHER PUBLICATIONS

Kuhne et al. Flow Cytometric Evaluation of Platelet Activation in Blood Collected Into EDTA vs. Diatube–H, American Jounal of Hematology 50: 40–45 (1995).*
Mody et al. Preanalytical requirements for flow cytometric evaluation of platelet activation: choice of anticoagulant, Transfusion Medicine 9: 147–154 (1999).*
Marcus et al. Identification of platelet proteins separated by two–dimensional gel electrophoresis and analyzed by MALDI–TOF and detection of tyrosine–phosphorylated proteins. ELECTROPHORESIS, Jul. 2000 21 (13) 2622–36) (Abstract, only).*
Beavis et al. (1996) Cytometry 24:390–5.
Becker et al. (1994) Coron.Artery Dis. 5:339–345.
Brostoff et al. (1998) Case Studies in Immunology. London, UK, Mosbey (Table of Contents), table of contents.
Cohen et al. (1987) Life Sci., 40:2445–2451.
Coller et al. (1993) Ann. N.Y. Acad. Sci., 614–193.
Conti et al. (1991) Clin.Chem., 37:1273–1275.
Dietz et al. (1996) Cytometry 23:177–186.
Furman et al. (1998) J.Am.Coll.Cardiol., 31:352–358.
Gurbel (2000) Am. Heart J., 139: 320–328.
Kühne et al. (1995) Am.J.Hematol., 50:40–45.
Matzdorff et al. (1998) Laboratory Hematology 4:163–168.
Michelson, (1994) Blood Coagul.Fibrinolysis, 5:121–131.
Mody et al. (1999) Transfus.Med. 9:147–54.
Mujumdar et al. (1989) Cytometry 10:11–19.
O'Connor et al. (1999) Am.J.Cardiol., 83:1345–1349.
Rinder (1998) Clin. Lab. Sci., 11:365–72.
Roederer et al. (1996) Cytometry 24:191–197.
Smith et al. (1976) J.Lab.Clin.Med. 88:167–72.
Tetta et al. (1997) Am. J. Kidney Dis. 30:S57–S65.
Violi et al. (1988) Haemostasis, 18:91–8.
Walton et al. (2000) Proc. SPIE–Int. Soc. Opt. Eng. 3926:192–201, IBOS Society of Photo–Optical Instrumentation Engineers.

* cited by examiner

*Primary Examiner*—Chris Chin
*Assistant Examiner*—Gailene R. Gabel
(74) *Attorney, Agent, or Firm*—Swanson & Bratschun, LLC

(57) ABSTRACT

The amount of platelet surface proteins in a sample may be measured by collecting a sample containing platelets into a collection tube containing a platelet stabilizing composition, labeling the platelet surface protein and detecting by cytometry.

20 Claims, 7 Drawing Sheets

METHOD FOR MONITORING RESTING AND ACTIVATED PLATELETS IN UNFIXED BLOOD SAMPLES

RELATED APPLICATIONS

This application claims the benefit of the priority of U.S. Patent Provisional Application Ser. No. 60/234,065, filed Sep. 20, 2000.

FIELD OF THE INVENTION

The present invention relates generally to a method for assaying platelets in whole blood without fixation. More specifically, the present invention relates to a method for measuring platelet count and phenotype in whole blood contacted with a platelet stabilizing composition, and analyzed using microvolume scanning laser cytometry (MLSC). In some preferred embodiments, the method comprises determining platelet count, expressed surface antigens and released soluble factors. In other embodiments, the method is used to diagnose medical conditions associated with defects in platelet function, and to perform stimulation assays (platelet functional tests). The present invention also encompasses kits comprising reagents for carrying out the method of the present invention.

BACKGROUND OF THE INVENTION

A growing number of diseases and syndromes are known to be associated with abnormalities in platelet number, function, or morphology. Classical platelet disorders, such as thrombocytopenia, have been joined by cardiac thrombosis, infectious pathologies and even Alzheimer's disease in the list of disorders associated with platelet abnormalities. See Gurbel, Am. Heart J., 139: 320–328 (2000); Tetta et al., Am. J. Kidney Dis., 30: S57–S65, (1997); Cohen et al., Life Sci., 40: 2445–2451 (1987).

In some cases, detection of the platelet abnormality may depend on determining the presence or absence of certain platelet surface antigens. For example, Glanzmann's Thrombasthenia is characterized by an absence of the GPIIb-IIIa complex (GPIIB/GPIIIA complex). Similarly, Bernard-Soulier syndrome is characterized by a deficiency in the GPIb-IX-V complex (CD42a–d). In other cases, the results of platelet functional tests, to evaluate the release of soluble markers and surface expression, are important. For example, the differential release of granule contents (such as CD62P and CD63) after various stimulation procedures may reflect deficiencies in the storage pools of the platelets.

As the number of associated pathologies grows, there is an increasing need to enumerate and characterize (i.e., "phenotype") platelets. Unfortunately, current methods for assaying platelets have a number of drawbacks. Automated platelet counters are available that can accurately determine the number of platelets in a sample. However, platelet counters do not provide information about expressed surface antigens or activation state of the platelets.

Measuring platelet aggregation and platelet-monocyte aggregation also provides potentially valuable information. Aggregometers, which measure platelet aggregation in response to various stimuli, provide information about platelet function and can be used to assess the efficacy of antiplatelet therapy. However, the most common activation procedures do not allow for the detection of soluble released materials or the characterization of platelet surface antigens.

Flow cytometry can be used to obtain important phenotypic information about platelets. The platelets in a sample can be directly counted. In addition, platelet surface markers can be identified and characterized through the use of fluorophore-labeled antibodies against specific cell surface antigens. However, use of flow cytometry to study platelets is limited by the reactive nature of the platelets themselves. Platelets may artificially become activated by exposure to the high-pressure fluidics system. To address this problem, flow cytometry phenotyping procedures typically include a fixation step to preserve the platelet sample. Although fixation eliminates the possibility of artificial activation, it also precludes the ability to subsequently stimulate and measure platelet responsiveness. See Matzdorff et al., Laboratory Hematology 4, 163–168, Carden Jennings Publishing Co., Ltd. (1998); Rinder, Clin. Lab. Sci., 11: 365–72, (1998); Furman et al., J. Am. Coll. Cardiol., 31:352–358 (1998); Michelson, Blood Coagul.Fibrinolysis, 5:121–131 (1994); Becker et al., Coron. Artery Dis., 5:339–345 (1994).

Sample fixation may also interfere with antibody binding to platelets. It is known that PAC-1 will not bind to paraformaldehyde-fixed platelets and that CD62P binding is decreased. Additionally, many of the substances used for fixation are toxic and require special handling. Exposure to formaldehyde, for example, may cause cancer.

To prevent the blood from clotting, it is standard practice to use anticoagulants with whole blood samples. Ethylenediamino-tetra-acetic acid (EDTA) is perhaps the most commonly used anticoagulant for hematologic studies. EDTA prevents coagulation by chelating calcium ions. The newer commercially available collection tube referred to as the CTAD tube (also known as Diatube H)—which includes the anticoagulant sodium citrate, and three inhibitors of platelet activation, theophylline, adenosine and dipyridamole—inhibits platelet activation. See Kuhne et al., Am. J. Hematol., 50:40–45 (1995); Mody et al., Transfus. Med., 9:147–154 (1999); O'Connor et al., Am. J. Cardiol., 83:1345–1349 (1999). Other combinations of platelet activation inhibitors may also be used. However, because of the forces involved in the fluidics of a cytometer, fixation is still recommended prior to examination on a cytometer. See Rinder et al. and Furman et al., supra.

In order to allow further activation studies, it is important to examine platelets in their "native" whole blood state without fixation. Thus, there is a need for an analytical procedure that allows activation and whole blood studies to be performed on the same sample. To measure both platelet surface antigens and soluble platelet activation products from the same sample, for example, would increase the total information content attainable from a sample.

Microvolume laser scanning cytometry (MLSC) provides a powerful method for monitoring fluorescently labeled cells in whole blood, processed blood, and other fluids. As with flow cytometry, fluorophore-labeled antibodies specific for cell surface antigens are used to identify, characterize and enumerate specific cell populations. The reaction can be done in whole blood and in general, there is no need to wash unbound reagent away. The cell-antibody mixture is loaded into an optical-quality capillary of known volume and analyzed with the laser-based fluorescence-imaging instrument. A small cylindrical laser spot is scanned across the stationary cells to produce an image of the entire capillary. Image-processing software is used to analyze the image and identify and enumerate the cells of interest. Because the interrogation volume of the capillary is known, absolute cell counts (cells per $\mu$l) are obtained. See, e.g., U.S. Pat. Nos. 5,547,849 and 5,556,764; Dietz et al., Cytometry 23: 177–186 (1996), each of which is incorporated herein by reference in its entirety. Importantly, such capillary cytometry eliminates the fluidic forces used in flow cytometry.

The SurroScan™ MLSC (SurroMed, Mountain View, Calif.) is able to classify and quantify hundreds of cell populations in small volumes of unprocessed whole blood and other biological fluids by detection of combinations of fluorophore-labeled antibodies to cell surface markers. See International Patent Application Serial No. PCT/US00/11133, entitled "Novel Optical Architectures for Microvolume Laser-Scanning Cytometers," published Mar. 2, 2000; Walton et al., *Proc. SPIE-Int. Soc. Opt. Eng.*, 3926:192–201 (2000) IBOS Society of Photo-Optical Instrumentation Engineers, both incorporated herein by reference in their entirety.

SUMMARY OF THE INVENTION

The present invention is directed to a method for assaying platelets in blood samples without fixation. The method involves the use of microvolume laser scanning cytometry (MLSC) to analyze blood samples that have been treated with anticoagulant containing inhibitors of platelet activation. Because the samples have not been fixed, the method can be used to gather multiple types of platelet information from the same sample, e.g., platelet count, phenotype and responsiveness. Such further information can be obtained via chemical assays, biochemical assays (e.g., ELISA) and even mass spectrometric analysis.

In another aspect, the present invention relates to methods for determining whether an individual has a reduced ability to form platelet thrombi and to a method of diagnosing Glanzmann's thrombasthenia, Bernard-Soulier syndrome, other platelet function defects or thrombocytopenia. The methods of the present invention are also applicable for the evaluation of platelets and platelet responsiveness following patient treatment, for example, studying the effect of a given therapeutic treatment.

In another aspect, the present invention relates to kits which are comprised of the reagents for carrying out the methods of the present invention.

DETAILED DESCRIPTION OF THE INVENTION

Figure 1A:
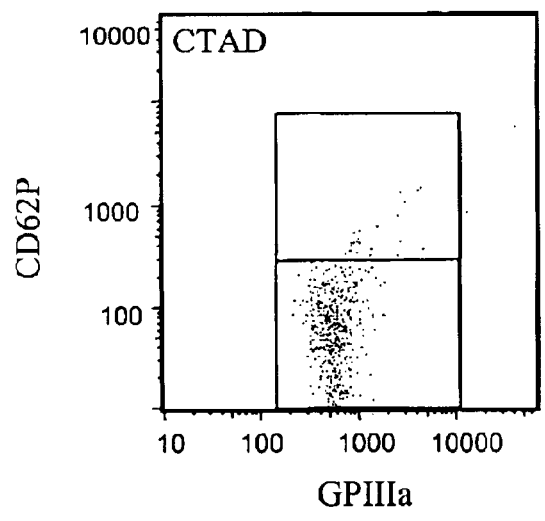
FIG. 1A shows a plot of expression of activation marker CD62P on platelets drawn into CTAD tubes.
Figure 1B:
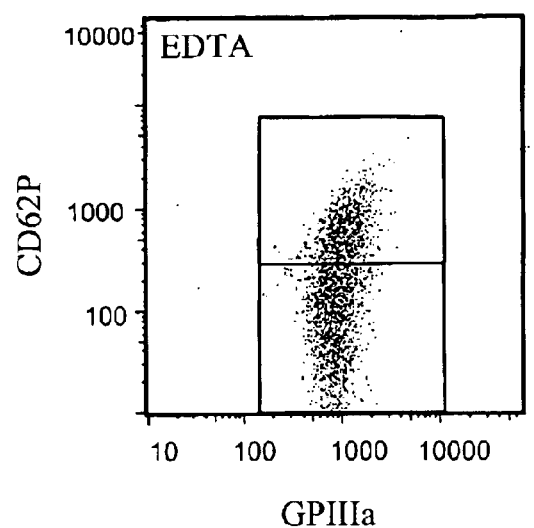
FIG. 1B shows a plot of expression of activation marker CD62P on platelets drawn into EDTA tubes.
Figure 1C:
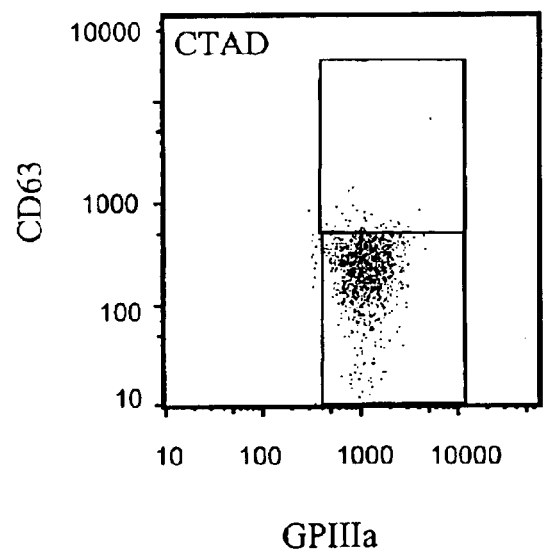
FIG. 1C shows a plot of expression of activation marker CD63 on platelets drawn into CTAD tubes.
Figure 1D:
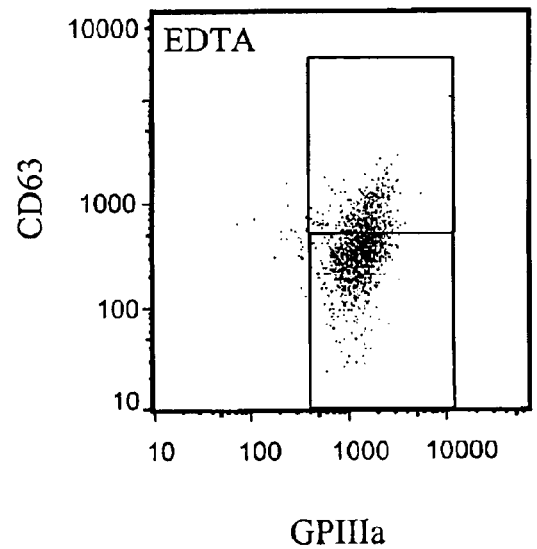
FIG. 1D shows a plot of expression of activation marker CD63 on platelets drawn into EDTA tubes.

The present invention is directed to a method for measuring platelet count and phenotype that can be performed simultaneously in the same blood sample without fixation. The method involves using a platelet stabilizing composition that has platelet inhibiting properties, preferably CTAD (citrate, theophylline, adenosine, dipyridamole), and analyzing the sample by microvolume laser scanning cytometry. In this way, platelets may be quantitated and phenotyped while maintaining a viable responsive state. In some embodiments, the method of the present invention includes the detection of labeled compound bound to platelets using MLSC.

In a typical embodiment, the method of the present invention involves obtaining a platelet-containing sample. Typically, the samples are of whole blood. However, the samples may also be of processed blood or any other platelet-containing fluid, including lymph and cerebrospinal fluid.

The sample is contacted with a platelet stabilizing composition to inhibit clot formation and prevent platelet activation during blood draw and sample handling. The platelet stabilizing composition comprises an anticoagulant and one or more platelet activation inhibitors. In preferred embodiments, the platelet stabilizing composition comprises citrate and one or more platelet activation inhibitors, preferably selected from the group consisting of adenosine, theophylline, dipyridamole and GPRP. In the most preferred embodiments, the platelet stabilizing composition is CTAD. The sample may be collected directly into a CTAD tube, or transferred to a CTAD tube after collection.

In processing the sample for conducting assays, the stabilized blood is typically mixed with a buffer, generally for purposes of dilution. A suitable buffer is capable of maintaining pH and salt concentration of the blood within a range suitable for platelet aggregation. Suitable pH levels are about 6.6 to 8.0, preferably, about 7.2 to 7.6, most preferably about 7.4. The buffer may be added to the blood as a solution or as a buffering composition in combination with salts. In some embodiments, the buffer comprises a platelet activation inhibiting factor. Suitable buffers include without limitation, Tyrode's buffer (a buffered salt solution containing glucose) (Sigma-Aldrich, St. Louis, Mo.), Tyrode's buffer containing theophylline and/or adenosine, phosphate buffered saline with 1% bovine serum albumin (PBS/BSA), HEPES buffer, and Tris buffer. In preferred embodiments, the buffer is Tyrode's buffer containing adenosine, theophylline, or both. Suitable concentrations of NaCl in the buffer are between 0.10M and 0.20M, preferably, about 0.15M. Other salts which may be used include $CaCl_2$. Suitable buffer concentrations of $CaCl_2$ range between about 0.1 mM to about 1.0 mM, preferably about 0.5 mM. Other suitable buffers will be readily determined by one of ordinary skill in the art.

In order to obtain information about expressed surface antigen the anticoagulated sample is incubated with a labeled compound that binds to the antigen under conditions that allow such binding to occur. In preferred embodiments, the labeled compound is an antibody. Monoclonal antibodies against surface antigens can be used to obtain precise measurements of the expression of those antigens. Such monoclonal antibodies include, but are not limited to, those against CD9 (p24), GPIIb/IIIb, GPIIIb/IIa, CD62P (P-selectin), CD63 (lysosomal antigen expressed on platelet surface after platelet activation), CD29 (integrin β1), GPIX, GPIba, CD36 (GPIIIb/IV), CD 49b(VLA-2), CD41b (GPIIb), CD43, CD100 and CD147.

By methods well-known in the art, the antibodies may be labeled with a fluorescent tag such as fluorescein, rhodamine, pycoerythrin, peridinin, chlorophyll protein (PerCP), allophycocyanin (APC), Cy5, Cy5.5, Cy7-APC and/or combinations thereof. Preferred fluorescent labels include Cy5, Cy5.5, Cy7-APC and/or combinations thereof. Other suitable fluorescent dyes will be readily determined by one of ordinary skill in the art.

In some embodiments, the methods of the invention include the addition of a fibrinogen cascade inhibitor to the whole blood sample. It is known that the tetrapeptide glycyl-L-prolyl-L-arginyl-L-proline (GPRP), an analog of the amino terminus of the α-chain of fibrinogen and the fibrin monomer, binds to fibrinogen and, under some experimental conditions, inhibits fibrin polymerization. Such inhibitory agents include molecules that mimic, in their fibrinogen binding property, the action of the amino terminal half of native human fibrinogen. These inhibitory agents are peptides, preferably those containing at least between two and twenty amino acid residues, and more preferably, peptides containing between four and ten amino acid residues. It is preferred that the peptide have at least 75% homology, and more preferably, 100% homology with a region contained in the amino terminal half of native human fibrinogen. GPRP is the currently most preferred inhibitory peptide. Another suitable inhibitory agent is an antibody capable of binding to the amino-terminal half of native human fibrinogen. Other suitable inhibitors will be readily determined by one of ordinary skill in the art.

In preferred embodiments, the prepared samples are analyzed by MLSC where fluorophore-labeled antibodies specific for cell surface antigens may be used to identify, characterize and enumerate specific cell populations. The same basic cell staining protocol is used for all of the MLSC studies. Cocktails of fluorophore-labeled antibodies specific for cell surface antigens are aliquoted at pre-determined concentrations and incubated with blood for a period of time. The cell-antibody mixture is diluted, loaded into an optical-quality capillary of known volume and analyzed with a laser-based fluorescence imaging. In order to reduce sample-handling steps and reduce variation among assays, it is preferred that MLSC assays use whole blood without any wash steps.

MLSC offers the advantages of being easy to use, requiring small sample volumes, having less manipulation of whole blood, and importantly, the ability to determine absolute cell counts. Further, because the diluted whole blood is placed into a stationary capillary with few or no manipulations and the laser scans the capillary, the platelets have less chance of being artificially activated. This is in contrast to flow cytometry where platelets are passed through high-pressure fluidics. Under such conditions, the platelets that have not been fixed may become activated and not reflect the in vivo resting/activation state of the platelets. Although fixation of the sample eliminates the possibility of artificially activating the cells by the fluidic systems of the cytometer, fixation does not allow for additional activation studies to be done concurrently on the same sample. The present invention has the additional advantage of requiring less than 5 µl and preferably less that 1 µl of blood per assay.

MLSC can be used to measure a large number of platelet surface antigens (in blood collected in CTAD tubes). These include CD9, CD29, CD36, GPIIB, GPIX, GPIb alpha, GPIIIA, CD62P and CD63, as well as other platelet antigens such as CD43, CD100 and CD147. Antigens that are expressed on cell types other than platelets can be monitored using a platelet specific counter stain, and the other cell types are easily diluted out of the measurement. A dilution of 1:10 to 1:1,000 is preferred, with a dilution of 1:100 most preferred. A 1:100 dilution of whole blood gives about <50 granulocytes per microliter compared to about 1,000 to about 3,000 platelets per µl in the same diluted sample. Using MLSC, activation independent antigens on the platelets, including without limitation CD9, CD29, CD36, GPIIB, GPIX, GPIb alpha, and GPIIIA, can be measured and determined at an average of $2.3 \times 10^5$ ($\pm 7 \times 10^4$) platelets per µl.

MLSC is often used to analyze white blood cell populations, granulocytes, monocytes, lymphocytes, and so on, in blood samples as conventionally obtained and processed. In such assays, many small, dim events are occasionally observed, especially when MLSC is used in homogeneous mode. This background fluorescence can interfere with the evaluation of the specific target cell populations. As demonstrated by specific staining with CD62P, the small, dim populations are mostly composed of activated platelets. The fluorescence is attributed to non-specific staining with antibody reagents and intrinsic fluorescence of the activated platelets. This effect can be reduced by appropriate sample handling methods, e.g., avoiding shaking of the sample, contact with certain plastics, and elevated temperatures (>25 to 37° C.). However, it is difficult to completely eliminate mechanical sources of platelet activation prior to MLSC analysis.

Contacting the sample with a platelet stabilizing composition according to the method of the present invention reduces this unwanted background in conventional MLSC. For example, collecting the blood into CTAD tubes minimizes platelet activation, and significantly reduces the dim events that interfere with the assay. Cellular assays for various white blood cell populations, granulocytes, monocytes, lymphocytes and the like, are improved when platelet activation is inhibited in this way. In addition to MLSC, the method of the present invention is useful in reducing unwanted fluorescent background in other types of cytometry, including with out limitation flow cytometry and Laser Scanning Cytometry (Compucyte Corp., Cambridge, Mass.).

The results of the platelet enumeration according to the methods of the present invention are consistent with published ranges. See Table III. Further, the percentage of activated platelets in the peripheral blood of normal individuals measured using the methods of the present invention (about 2%) is consistent with reported values obtained using formaldehyde-fixed samples and flow cytometry. Corash, Blood Cells, 16: 97–106 (1990). Also in agreement with previous data on fixed platelets, less than about 2% of platelets from the whole blood of normal individuals expressed the activation markers CD62P or CD63. However, after in vitro thrombin activation, about >93% of the platelets expressed CD62P and CD63.

In one preferred embodiment, the method comprises collecting a sample containing platelets in a CTAD tube. The sample is then incubated with a labeled antibody that specifically binds platelets, under appropriate conditions (e.g., those that will permit binding). The sample is diluted with Tyrode's buffer (containing theophylline and/or adenosine) and loaded into Flex32™ capillary array and analyzed by Surroscan™ MLSC. The assays are done in homogeneous mode, without removal of unbound reagent. After all dilutions, the fluorescent platelet counts per capillary are about 1,000–2,000; this is comfortably in the range of 10 to 12,000 that is appropriate for the cytometry. This platelet count level provides appropriate counting statistics and minimizes platelet-platelet overlap that can occur at higher platelet concentrations. Images are converted to flow cytometry standard (fcs) format with in-house software and analyzed with FlowJo™ cytometry analysis software (Tree Star, Inc., San Carlos, Calif.). Fluorescence intensities are compensated for spectral overlap of the dyes.

Also contemplated in the present invention are kits that include reagents in amounts sufficient to perform at least one assay. In a preferred embodiment, the kit comprises a first container comprising a labeled compound, such as a monoclonal antibody labeled with a fluorescent dye, a second container comprising a collection tube containing a platelet stabilizing composition; and a third container comprising a buffer solution. In a highly preferred embodiment, the platelet stabilizing composition is CTAD, and the buffer is Tyrode's buffer containing adenosine and/or theophylline. Instructions for use of the packaged kit typically may also be included. In one preferred embodiment, the kit contains reagents sufficient to assay for the presence of activated and resting platelets in a sample, and can be used to identify persons at risk of a thrombotic event.

Still another embodiment of the present invention relates to a method of diagnosing individuals with defects in platelet function, including a method of diagnosing and monitoring Glanzmann's thrombasthenia, Bernard-Soulier syndrome, other platelet function defects or thrombocytopenia in an individual. For example, individuals who are homozygous for Glanzmann's thrombasthenia have virtually no functional GPIIb/IIIa receptors and have prolonged bleeding times. Individuals who are heterozygous for Glanzman thrombasthenia have at least 50–60% of the normal number of GPIIb/IIIa receptors but show normal bleeding times. See, e.g., Coller et al., Ann. N.Y. Acad. Sci., 614:193 (1993). Individuals with Bernard-Soulier syndrome have a deficiency in the expression of the GPIb-IX-V complex (CD42 a-d). Another embodiment of the invention relates to a method for diagnosing thrombocytopenia. Individuals with platelet levels of below about 100,000 platelets/µl are severely thrombocytopenic and also have prolonged bleeding times.

According to the method of the present invention, a blood sample is first obtained from the subject being assessed for the defect in platelet function. The blood sample is then contacted with a platelet stabilizing composition, preferably by collection into a CTAD tube, and a dilution buffer containing inhibitors of platelet activation sufficient to maintain the pH and salt concentration of the anticoagulated blood within a range suitable for platelet aggregation. The stabilized, buffered blood sample is incubated with a labeled compound, typically a labeled antibody, which specifically binds platelets under conditions that will allow the compound to bind with its target. The sample may be agitated. Finally, the labeled compound bound to platelets is detected using MLSC.

In addition to diagnosing patients suffering from a defect in platelet function, the method of the present invention may also be used to monitor the effectiveness of a therapeutic agent being administered as a treatment for such defect in platelet function. In addition, the method of the present invention may be used to evaluate whether a given therapeutic treatment can lead to an abnormality in platelet number, function or morphology or an improvement in any defect in platelet function.

For the diagnosis of Glanzmann's thrombasthenia, the labeled compound is one that specifically binds the GPIIb-IIIa complex. Likewise, for the diagnosis of Bernard Soulier syndrome, the labeled compound is one that specifically binds the GPIb-IX-V complex. The method of the present invention is preferably performed when the individual has not been administered an agent that blocks surface protein receptors.

Importantly, the present invention allows evaluation of both the resting phenotype and measurement of the responsiveness of the platelets from the same samples to activation agents using the cell surface markers of CD62P and CD63. FIG. 5; Table III. Although thrombin was used in the examples, other platelet agonists or activators such as ADP or the thrombin receptor-activating peptide (TRAP) can be used to measure the effects of various drugs or disease states on sub-optimal platelet stimulation. See Rinder et al. and Furman et al., supra. Other platelet stimulating agents include without limitation collagen, ristocetin, botrocetin, epinephrine, arachidonic acid and its metabolites, platelet activating factor, plasmin, serotonin, vasopressin, thrombin, tissue plasminogen activator, streptokinase and immune complexes, adenosine diphosphate, collagen, ristocetin, botrocetin, epinephrine, arachidonic acid and its metabolites, platelet activating factor, plasmin, serotonin, vasopressin, tissue plasminogen activator, streptokinase and immune complexes.

The method of the present invention, whereby whole blood is drawn into a CTAD tube and diluted with a buffer containing a platelet activation inhibiting factor is useful for analysis of platelets by means other than MLSC. The unfixed, stabilized blood sample may be used in other types of cytometry, including with out limitation flow cytometry and Laser Scanning Cytometry (Compucyte Corp., Cambridge, Mass.) to achieve the advantages of the present invention.

Figure 6A:
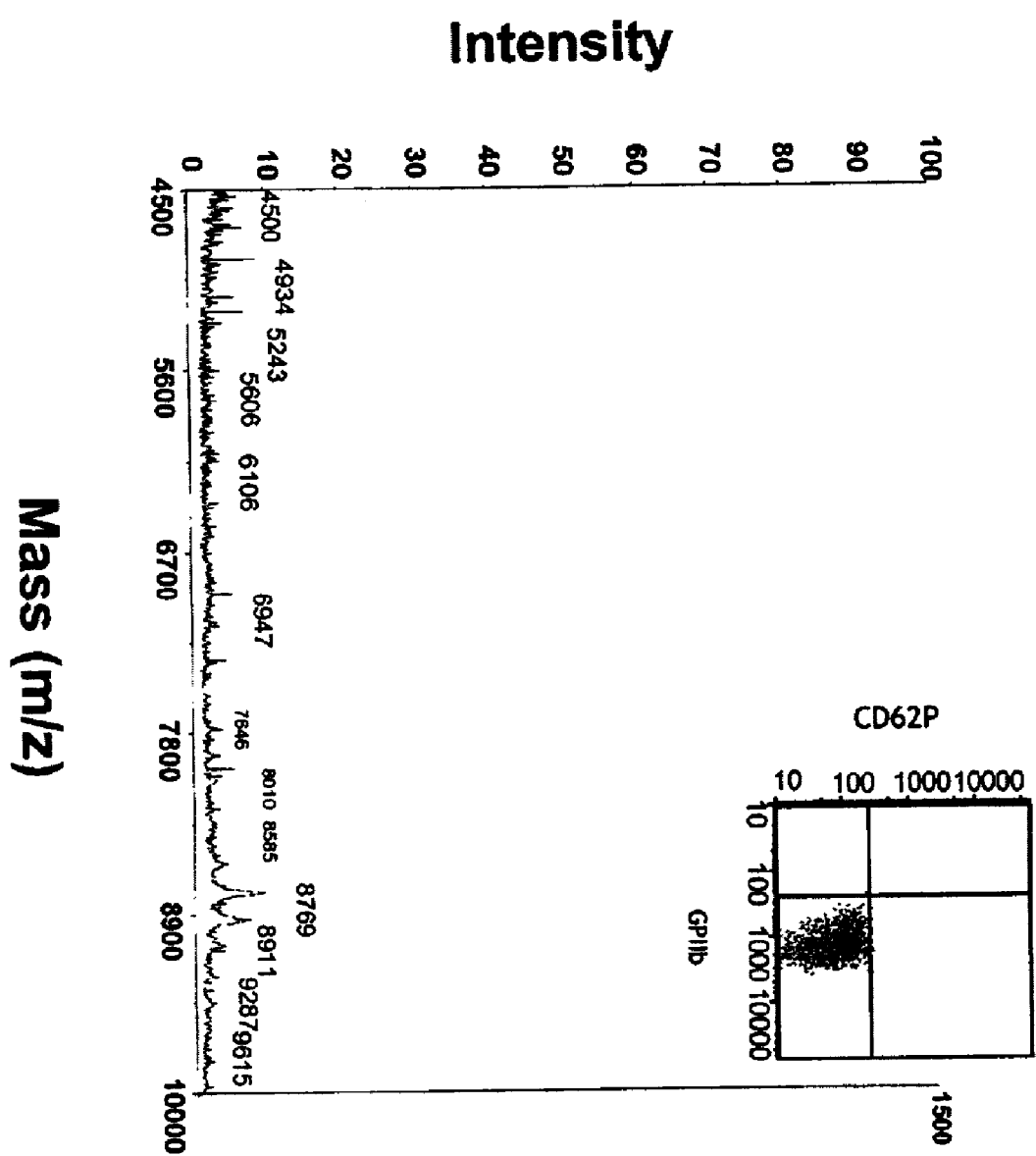
FIG. 6 shows the integration of MLSC and MALDI-TOF MS analysis of material released from platelets with (A) and without (B) thrombin.
Figure 6B:
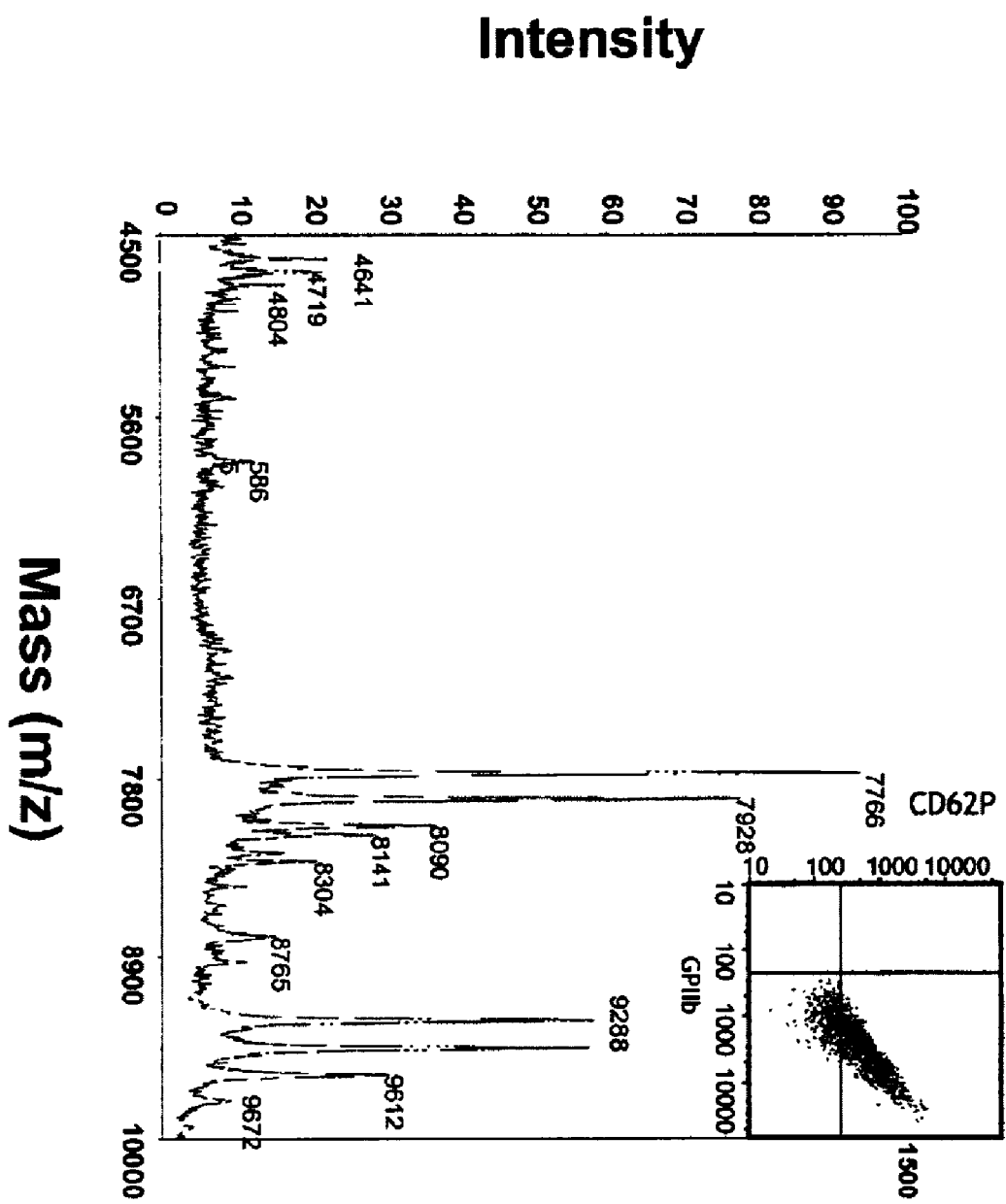

The method of the present invention, in which the sample is contacted with a platelet stabilizing composition is also beneficial in conjunction with assays that can be performed in addition to MLSC. For example, ELISA assays and mass spectrometric assays of whole blood soluble factors benefit from the use of the method of the present invention. For example, MALDI-TOF mass spectrometric analysis of a whole blood sample of stimulated and non-stimulated platelets can be performed, while the same samples can be evaluated by MLSC to determine the percent of platelet activation. An example of such integrated analysis is shown in FIG. 6.

The following specific examples are provided to better assist the reader in the various aspects of practicing the present invention. As these specific examples are merely illustrative, nothing in the following descriptions should be construed as limiting the invention in any way.

EXAMPLES

In the following examples, human blood samples were obtained from normal volunteers and processed within 2 to 48 hours, depending upon experimental conditions. Researchers were completely blinded to all information regarding the volunteers. Phosphate buffered saline with 1% BSA (PBS/BSA), thrombin and Glycine-Proline-Arginine-Proline (GPRP) were all obtained from Sigma-Aldrich (St. Louis, Mo.). The small organic dyes Cy5 and Cy5.5 can be coupled to the amino groups of antibodies using single-step NHS chemistry and well established procedures. Mujumdar et al., Cytometry 10:11–19 (1989). The tandem dye, Cy7-APC, has been previously described and is linked to the sulfhydryl groups of moderately reduced antibody in a 3-step procedure using the heterobifunctional crosslinking reagent SMCC. See Roederer et al., Cytometry 24:191–197 (1996); Beavis et al., Cytometry 24:390–5 (1996). Anti-CD9, GPIIB, GPIIIA, CD62P, and CD63 monoclonal antibodies were obtained from PharMingen (San Diego, Calif.). The anti-CD29 monoclonal was obtained from Serotec (Raleigh, N.C.), and the anti-GPIX and GPIb alpha were obtained from Beckman-Coulter. CTAD and EDTA tubes were obtained from BD-Vacutainer Systems.

Preparation of platelet rich plasma and washed platelets. Platelet rich plasma was prepared from the CTAD tubes by removing 4 ml of whole blood and centrifuging at 100×g for 15 minutes. Smith et al., J. Lab. Clin. Med., 88: 167–72 (1976). The platelets were pelleted by centrifuging in an Eppendorf micro-centrifuge for 10 minutes at 1000×g. Plasma was removed from the platelet pellet and 1 ml Tyrode's buffer (containing platelet activation inhibitors) was gently added back without disturbing the platelet pellet. Without re-suspending the pellet, the buffer was removed and a volume of Tyrode's buffer equal to the starting PRP plasma was added and the pellet was re-suspended. Kuhne et al., Am J Hematol 50:40–5 (1995).

Plasma preparation. Plasma, for examination of malondialdehyde-like (MLM) material and platelet factor-4 (PF4), was prepared from both CTAD and ethylene diamine tetraethylacetate (EDTA) anti-coagulated blood, drawn from the same individual by transferring the blood to a 15 ml conical centrifuge tube and centrifuging at 1000×g (room temperature) for 15 minutes. Plasma was either transferred to a Nunc cryogenic freezing tube for storage at $-80°$ C. or used immediately.

Platelet stimulation. Thrombin stimulation was carried out on either washed platelets or 1:10 diluted whole blood in the presence of the fibrinogen cascade inhibitor peptide glycine-proline-arginine-proline (GPRP, 2 mM final concentration). Thrombin (5 U/ml) was added to 10 µl of sample in 75 µl Tyrode's buffer containing the GPRP (final total volume of 100 µl). Because the CTAD tubes contain reversible inhibitors of platelet activation, it was initially determined that a 10-fold dilution of the whole blood was sufficient to reduce the inhibitors below effective concentration and permit stimulation. Under the experimental conditions used (i.e., thrombin stimulation), further dilution did not add any additional benefit to reducing the effects of the CTAD tube inhibitors. Next, the reaction was incubated in a 37° C. water bath for 5 or 10 minutes and subsequently diluted to 1000 µl (1:100) with Tyrode's buffer supplemented with 1.5 mM theophylline and 0.37 mM adenosine (final concentration). In order to stop the stimulation and prevent non-specific activation of the control and test samples caused by the handling and staining techniques, theophylline and adenosine were added to the samples. A control sample lacking only the thrombin was run in parallel.

Determination of Malondialdehyde-like material and Platelet Factor-4. The determination of malondialdehyde-like material (MLM) was done using the thiobarbutaric acid reaction. Violi et al., Haemostasis, 18:91–8 (1988); Conti et al., Clin.Chem., 37:1273–1275 (1991). A 100 µl trichloroacetic acid (TCA) precipitated sample, made by diluting the sample 1:2 in 20% TCA, was placed into a 96 well Thermowell (polycarbonate, Corning) plate followed by the addition of 0.2 volumes of 0.12 M thiobarbutaric acid (TBA) (20 µl) (Sigma-Aldrich). A malondialdehyde standards made by diluting from 1 µM acid activated (1,1,3,3) tetramethoxypropane (Sigma-Aldrich) down to 15.625 nM in PBS was also run in parallel. The reaction was incubated in an oven at 70° C. for 30 minutes then allowed to cool for 5 minutes. The sample reaction and standards were transferred to a Corning white opaque 96 well flat bottom plate and read on a Wallac Victor plate reader (Perkin-Elmer Lifesciences, Gaithersburg, Md.) using an excitation wavelength of 525 nm and an emission wavelength of 560 nm. The assay sensitivity is 10 nM and the range is 10–1000 nM). Platelet Factor 4 was measured by chemiluminescent using ELISA. Antibodies were obtained from U.S. Biologicals (Swampscott, Mass.) and Affinity Biologicals Enzyme Research Lab. (South Bend, Ind.), recombinant standard from Chemicon (Temecula, Calif.). Briefly, Corning black opaque 96 well microtiter plates were coated with rabbit polyclonal anti-PF4 (human) overnight at 4° C. Plates were washed and samples or standards were added to the wells and allowed to incubate at room temperature. After washing, biotinylated polyclonal sheep anti-PF4 (human) was added followed by washing and the addition of avidin-alkaline Phosphatase. Plates were washed and the CDP-Star® (Tropix, Bedford, Mass.)) substrate added, allowed to develop and read on the Wallac Victor plate reader. The assay sensitivity of the assay is 20 pg/ml.

Staining for MLSC. For whole blood platelet stains, 10 µl of whole blood was diluted into 990 µl of Tyrode's buffer supplemented with 1.5 mM theophylline and 0.37 mM adenosine for a final dilution of 1:100. Twenty microliters of diluted whole blood, thrombin-stimulated samples, or control samples were added to 96 well micro-titer plates containing 5 µl of the appropriate reagent cocktail. The cells were incubated in the dark at room temperature for 20 minutes. At the end of the incubation, 50 µl of modified PBS/BSA buffer supplemented with theophylline (1.5 mM)/ adenosine (0.37 mM) (to prevent activation), and Zwittergent® (50 mM) was added to all the wells and mixed thoroughly. Twenty-one microliters of diluted sample was loaded into Flex32 capillary array and analyzed by Surroscan MLSC. The assays are performed in homogeneous mode, without removal of unbound reagent. After all dilutions, the fluorescent platelet counts per capillary are about 1,000–2,000, comfortably in the range of 10 to 12,000 that is appropriate for the cytometry. This platelet count level provides appropriate counting statistics and avoids coincident events. Images were convened to flow cytometry standard (fcs) format with in-house software and analyzed with FlowJo™ cytometry analysis software (Tree Star, Inc., San Carlos, Calif.). Fluorescence intensities are compensated for spectral overlap of the dyes.

Example 1

Comparison of CTAD and EDTA for use in MLSC

Previous research has shown that addition of platelet inhibitors to the anti-coagulant greatly reduces the activation state of human platelets prior to testing. Kuhne et al., Am. J. Hematol. 50:40–5 (1995); Mody et al., Transfus.Med. 9:147–54 (1999). To evaluate the platelet inhibition provided by CTAD anticoagulant in the MLSC format, whole blood drawn into CTAD tubes was compared to whole blood drawn into EDTA tubes. Blood was obtained from a volunteer (set of 5 volunteers) and processed within 4 hours. This was done without fixation in order to maintain epitope integrity and allow for further activation studies. The samples were incubated with antibodies against platelet surface activation markers CD62P and CD63, as well as antibodies against GPIIIA, an antigen present on all platelets. All platelets were identified with GPIIIa (Cy5.5). The sample was then analyzed using MLSC. Gates for the Cy5-CD62P and Cy5-CD63 positive events were drawn based upon MOPC-21 control antibody staining.

FIG. 1 shows plots of the activation markers versus GPIIIA. The fraction of platelets expressing both CD62P and CD63 is significantly higher in the blood drawn into EDTA tubes. The platelet activation results on matched EDTA and CTAD blood samples analyzed over 48 hours are summarized in Table I. At all time points, the platelets in blood drawn into EDTA tubes show greater activation than those in the blood drawn into CTAD tubes. This difference can be measured both by the fraction of activated platelets and by mean fluorescence intensity. For instance, about 40–50% of the platelets are positive for CD62P in the EDTA sample, as opposed to only about 4–7% in the CTAD sample.

The relatively broad range of platelet activation levels observed with the EDTA samples (about 8 to 50%) suggests that variation in handling during blood draw, transport and analysis can affect the results. Most EDTA samples have substantial platelet activation, especially at later time points. For blood collected into CTAD tubes, there was little change in the low level of expression of CD62P (7.4±2.8% versus 4.4±0.89%) or CD63 (unchanged) over 48 hours. There were also no observable differences in the expression of the pan surface antigens CD9 or GPIIIA on platelets between the EDTA and CTAD samples. The mean fluorescence intensity of GPIIB, however, was about 40% lower in EDTA compared to CTAD, suggesting a dependence on divalent cations (EDTA is a stronger chelator of divalent cations than is citrate). There was no significant difference in the total platelet counts with the two anticoagulants (p<0.95). The total platelet count did not change significantly from 4 to 48 hours in the CTAD tubes (p<0.5). However, there was a small but significant decrease in platelet count from 4 to 48 hours in the EDTA tubes (p<0.05).

TABLE I

Activation markers CD62P and CD63 on matched samples drawn into EDTA and CTAD tubes.

| | Time from draw | % Positive EDTA | % Positive CTAD | Mean Intensity EDTA | Mean Intensity CTAD |
|---|---|---|---|---|---|
| CD62P | <4 hr | 37 ± 17* | 4.4 ± 0.9 | 1110 ± 230* | 710 ± 130 |
| | 24 hr | 49 ± 20* | 6.3 ± 1.0 | 910 ± 130 | 760 ± 120 |
| | 48 hr | 41 ± 4.8* | 7.4 ± 2.8 | 900 ± 60* | 770 ± 61 |
| CD63 | <4 hr | 22 ± 20* | 4.6 ± 1.7 | 760 ± 43* | 630 ± 62 |
| | 24 hr | 37 ± 22 | 5.5 ± 2.9 | 690 ± 77 | 640 ± 55 |
| | 48 hr | 15 ± 7.0* | 4.6 ± 1.7 | 680 ± 42 | 684 ± 120 |

*indicates that there is a significant difference between EDTA and CTAD tubes, p < 0.05 by paired t-test.

In Table I, each result is the average of 5 subjects, except for the 24-hour points, which are averages of 4 measurements. The matched samples, EDTA and CTAD are used from each subject. The platelets are identified with the marker GPIIIA. Mean relative intensity is for the entire platelet population.

To further evalute platelet activation, both platelet factor 4 (PF4) and malondialdehyde-like material (MLM) were measured in plasma prepared from matched EDTA and CTAD samples. Samples were obtained from 5 individuals whose blood was first drawn into EDTA followed immediately by a second draw into CTAD. PF4 expression was determined by ELISA (sensitivity of 20 pg/ml). When averaged, PF4 for EDTA was 627±449 pg/ml and CTAD was 108±48 pg/ml (p<0.05). MLM was measured using a TBA reaction. When averaged, the results are 91±28 (EDTA) versus 44±24 nM (CTAD) MLM, p<0.0001.

Figure 2A:
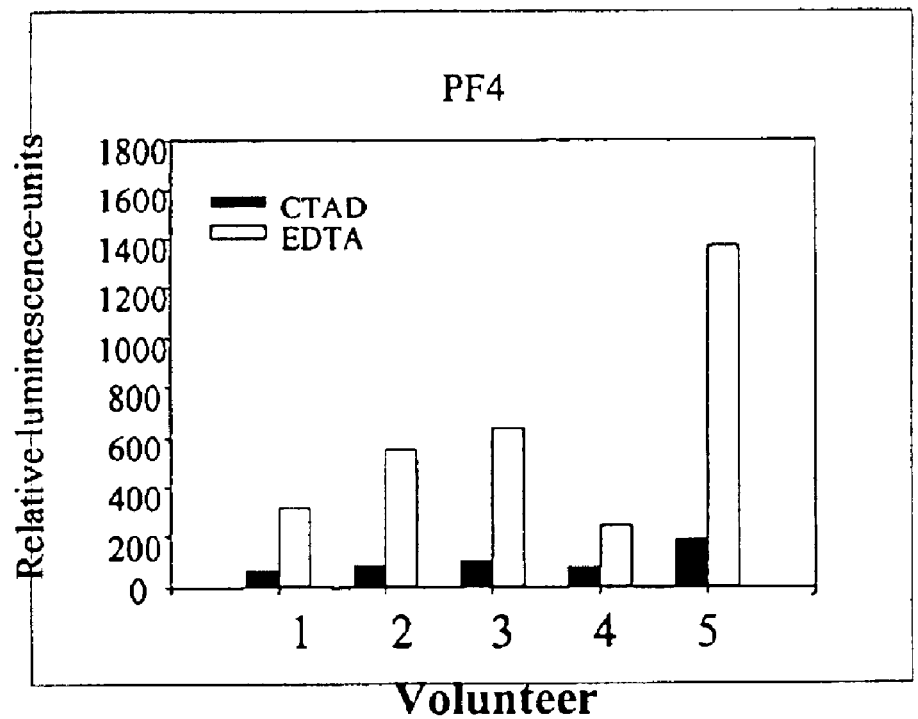
FIG. 2A shows a plot of expression of platelet factor 4 (PF4) in plasma drawn into either CTAD tubes or EDTA tubes.
Figure 2B:
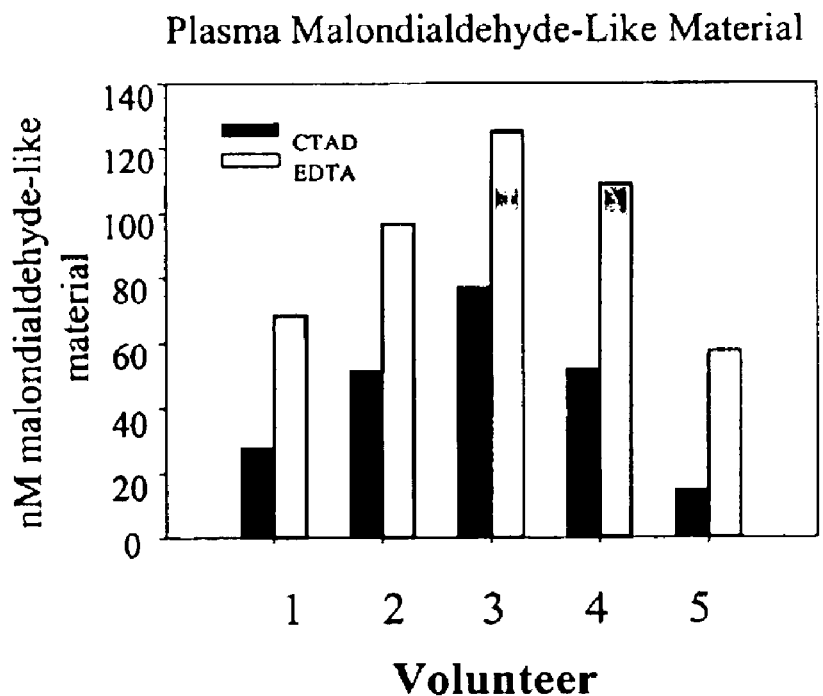
FIG. 2B shows a plot of expression of malondialdehyde-like material (MLM) in plasma drawn into either CTAD tubes or EDTA tubes.
Figure 3A:
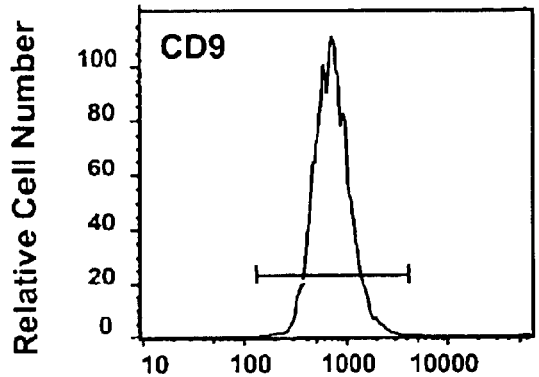
FIG. 3A shows a plot of the expression of platelet surface antigen CD9 in blood drawn into CTAD tubes.
Figure 3B:
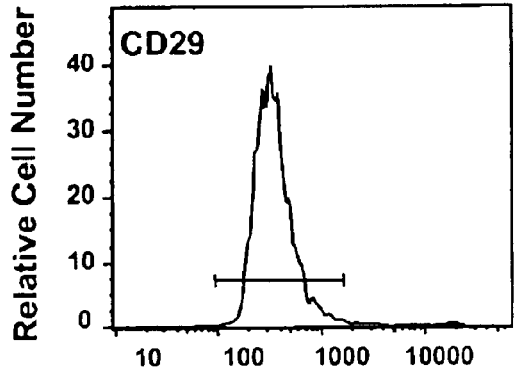
FIG. 3B shows a plot of the expression of platelet surface antigen CD29 in blood drawn into CTAD tubes.
Figure 3C:
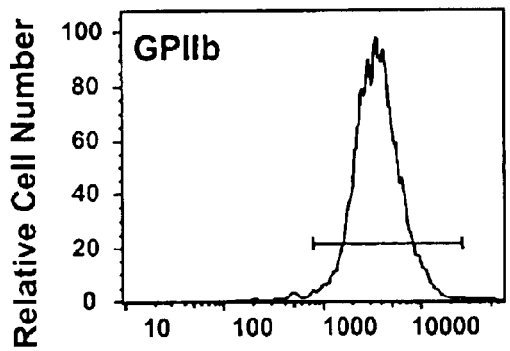
FIG. 3C shows a plot of the expression of platelet surface antigen GPIIb in blood drawn into CTAD tubes.
Figure 3D:
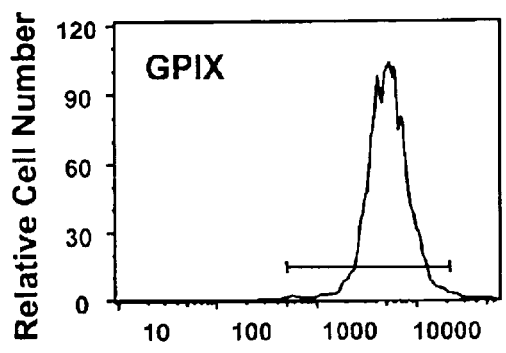
FIG. 3D shows a plot of the expression of platelet surface antigen GPIX in blood drawn into CTAD tubes.
Figure 3E:
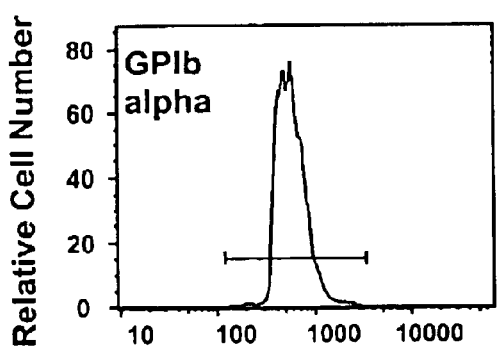
FIG. 3E shows a plot of the expression of platelet surface antigen GPIb alpha in blood drawn into CTAD tubes.
Figure 3F:
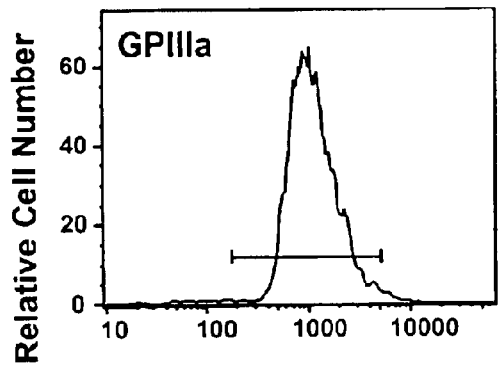
FIG. 3F shows a plot of the expression of platelet surface antigen GPIIIa (F) in blood drawn into CTAD tubes.

As shown in FIG. 2A, PF4 release was 5 times greater in the EDTA samples than in the CTAD samples (p<0.05). Similarly, there was a significantly higher amount of MLM present in the plasma of the EDTA sample than in the plasma of the CTAD. This is shown in FIG. 2B. The higher levels of soluble factors in the EDTA samples were observed for all matched pairs. The elevated levels of these soluble factors correlated with the higher level of CD62P expression on blood collected into EDTA tubes. All of the surface staining and biochemical results are consistent with a higher activation state for platelets in the blood drawn into the EDTA versus CTAD tubes. All subsequent procedures were performed using blood drawn into CTAD tubes. This result demonstrates that blood collection with CTAD tubes allowed labeling platelets without the need for fixation in MLSC.

Example 2

Pan Platelet Markers for MLSC

Using blood collection with CTAD tubes, and no fixation, the surface expression of various platelet surface antigens using the MLSC format was examined. Antigens were analyzed for CD9, CD29, CD36, GPIIB, GPIX, GPIb alpha, GPIIIA, CD62P, CD63. Information regarding these surface antigens is provided in Table II. Representative examples of antigen staining in a single parameter stain (i.e., one color) are shown in FIG. 3A–F. Whole blood was diluted 1:100 in Tyrode's buffer containing inhibitors of platelet activation (theophylline and adenosine). MOPC-21 control antibody staining showed little or no positive events (data not shown). As shown, CD9 and GPIIB were labeled with Cy5.5, GPIIIa with Cy7-APC and all others with Cy5.

TABLE II

Platelet Antigens

| Antigen | Clone | Distribution | Description |
|---|---|---|---|
| CD9 | M-L13 | Pan | Tetraspanin involved in adhesion and activation |
| CD29 | 3S3 | Platelets, broad tissue dist. | Integrin β1 - involved in adhesion of platelets via VCAM and MadCAM-1. |
| CD36 | CB38 | Platelets and monocytes, etc. | GPIIIb/GPIV scavenger receptor for oxidized LDL binds HDL, LDL, VLDL as well as thrombospondin-1 and collagen. |
| GPIIB | HIP8 | Platelets and megakaryocytes | GPIIb-glycoprotein which forms a dimer with GPIIIb; binds fibrinogen upon activation. |
| GPIX | SZ1 | Platelets and megakaryocytes | GPIX - the CD42 complex is the major complex involved in the early adhesion of platelets to damaged vessel wall under high stress condition; receptor for von Willebrand factor. |
| GPIb alpha | SZ2 | Platelets and megakaryocytes | GPIbα portion of the CD42 complex. |
| GPIIIA | S221 | Platelets, megakaryocytes, endothelial, oestioclasts | GPIIIb-glycoprotein which forms a dimer with GPIIa on platelets; binds fibrinogen upon activation. |
| CD62P | AK4 | Activated platelets | Protein found in the alpha granules of platelets involved in the adherence of platelets to other cells, surface expression observed only after activation. |
| CD63 | H5C6 | Activated platelets | Protein found in the platelet dense granules, surface expression only after activation. |

Figures 4A, 4B:
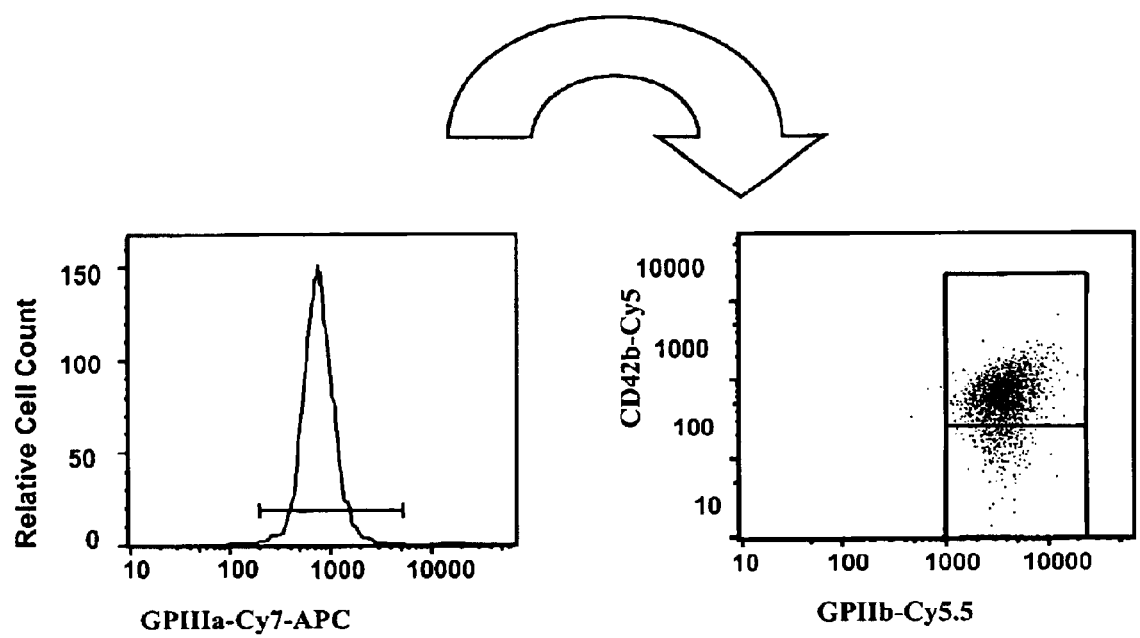
FIG. 4A shows a plot of three-color staining (Cy5, Cy5.5, and Cy 7-APC) on whole blood drawn into CTAD tubes in which gating was placed on total GPIIIA positive events.
FIG. 4B shows shows a plot of three-color staining (Cy5. Cy5.5. and Cy 7-APC) on whole blood drawn into CTAD tubes in which all events which are GPIIIA positive.

All platelets were found to be positive for CD9, CD29, GPIIB, GPIX, GPIb alpha and GPIIIA. The relative high intensity staining for the antigens GPIIB, GPIX, and GPIIIA, in combination with the fact that GPIIB and GPIX are specific for platelets, allow use of these antigens as pan platelet markers in 2 and 3-color (multi-antigen) stains. Cy5 is a brighter fluorescent tag than Cy5.5 or Cy7-APC and is best used for lower copy number surface antigens and activation antigens, such as CD62P and CD63. A representative example of a Cy5, Cy5.5, and Cy7-APC three-color combination is shown in FIGS. 4A–B. Whole blood from 20 volunteers was drawn into CTAD tubes and diluted 1:100 with PBS-1% BSA containing inhibitors of platelet activation. In that example, gating was first placed on total GPIIIA positive events (anti-GPIIIA-Cy7-APC) (FIG. 4A). Therefore, all events in the 2-parameter histogram (FIG. 4B) are GPIIIA positive. Because the MLSC format does not rely on scatter characteristics of the events, there are essentially no events recorded in the MOPC control (i.e., no events detected over a blank run capillary). The specificity of the surface staining is demonstrated by the lack of cell staining using Cy5, Cy5.5, and Cy7-APC conjugated MOPC-21 antibody (i.e. the absence of any events). As shown in FIGS. 4A–B, all of the GPIIIA positive events also express the platelet specific antigens of GPIIB and GPIb alpha.

Platelet results obtained from normal healthy volunteers and results are summarized in Table III. All of the pan-platelet surface antigens gave consistent total counts of about 230,000 platelets per $\mu$l. The range of about 100,000 to about 360,000 was observed among the different individuals. There were no significant differences among the six surface antigens. Linear regression for each pair of antigens yielded straight lines with slopes within 10% of 1 and regression coefficients near 1 ($r^2>0.9$). Moreover, the total platelet counts were consistent with literature normal ranges of about 150,000 to about 400,000 platelets per $\mu$l. See e.g., Kuhne, T. et al, Am. J. Hematol 50: 40–45 (1995); Mody, M. et al., Transfus. Med. 9: 147–154 (1999); O'Connor, C. M. et al., Am. J. Cardiol., 83: 1345–1349 (1999).

TABLE III

Platelet Enumeration Results

| Antigen | Observed (platelets/$\mu$l) | % of total platelets* | Expected (platelets/$\mu$l or %) |
|---|---|---|---|
| Total | | | |
| CD9 | 231,000 ± 69,000 | | Total platelet count of 150,000–400,000 1 as determined by platelet counters |
| CD29 | 242,000 ± 72,000 | | |
| GPIIB | 237,000 ± 72,000 | | |
| GPIX | 237,000 ± 72,000 | | |
| GPIb alpha | 216,000 ± 83,000 | | |
| GPIIIA | 230,000 ± 72,000 | | |
| Activated | | | |
| CD62P (whole blood) | 3930 ± 3570 | 1.7 ± 1.4 | 1–2% |
| CD62P (thrombin) | 192,000 ± 53,000 | 92 ± 3.1 | >95% |
| CD62P (activation control) | 10,400 ± 8,200 | 5.4 ± 4.5 | <10% |
| CD63 (whole blood) | 5100 ± 3300 | 2.3 ± 1.5 | 1–2% of total |
| CD63 (thrombin) | 142,000 ± 40,000 | 72 ± 8.2 | >80% |
| CD63 (activation control) | 9200 ± 5500 | 5.1 ± 4.2 | <5% |

The results in Table III are the average of 19 to 22 subjects. The total values are from a single parameter gate. The activation results are from a 3-color assay with Cy5-GPIIIA, Cy7APC-GPIIBa and either Cy5-CD62P or Cy5-CD63. Percent (%) activation is calculated within each assay. The total platelet count of 150,000–400,000 was determined by platelet counters. See e.g., Kuhne T. et al., Am J Hematol., 50: 40–45 (1995); Brostoff J. et al., Case Studies in Immunology. London, UK, Mosbey (1998). The results indicate that with respect to the present invention, GPIIB, GPIX, and GPIIIA are the best pan platelet markers.

Example 3

Platelet Activation

Figure 5A:
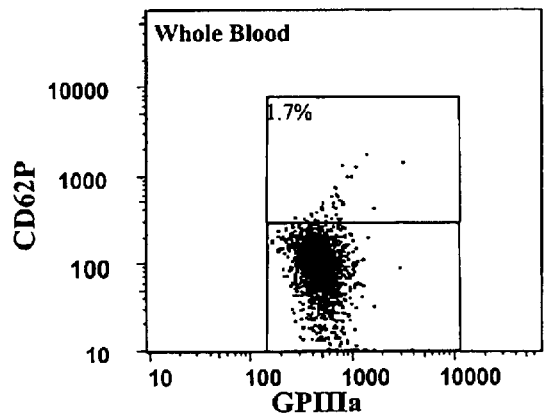
FIG. 5A shows a representative example of the expression of the activation marker CD62P in whole blood

The present invention can be used to measure the activation state of platelets or changes in the ability of platelets to respond to activation. The expression of surface antigens CD62P and CD63 increases after thrombin activation. Critical to the study of platelets is the ability to either detect activated circulating platelets or changes in the ability of platelets to respond to activation stimuli. The levels of circulating CD62P and CD63 positive platelets in resting and stimulated whole blood was examined. Whole blood samples from 20 volunteers were drawn into CTAD and tested less than 4 hours after collection. The whole blood was first diluted 1:10 in the presence of GPRP and without or with thrombin (5 U/ml). After a 5 minute activation the sample is further diluted 1:10 for a final dilution of 1:100. Cy5.5-GPIIIA was used to identify all platelets. Gates for the Cy5-CD62P and Cy5-CD63 positive events were drawn based upon Cy5-MOPC-21 control antibody staining. The stain in the absence of thrombin acts also as a further control for the stimulation assay. As shown in FIGS. 5A and D, the expression of both CD62P and CD63 was limited to less than about 2% of the total platelets (GPIIB$^+$, GPIIIA$^+$) in fresh whole blood. This was consistent with the results in shown in FIG. 1. Among all 20 samples, there was consistently no or little platelet activation by CD62P or CD63 (2%) for the whole blood analysis.

Figure 5B:
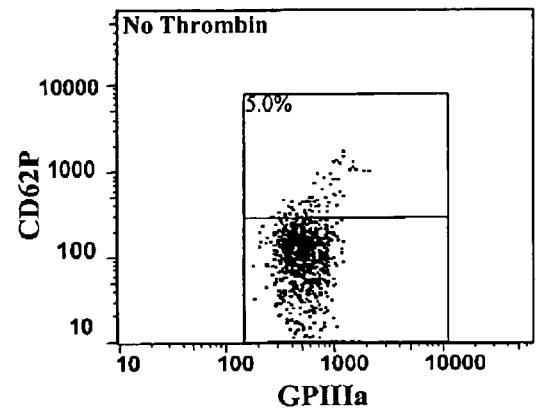
FIG. 5B shows a representative example of the expression of the activation marker CD62P in blood activated without thrombin.
Figure 5C:
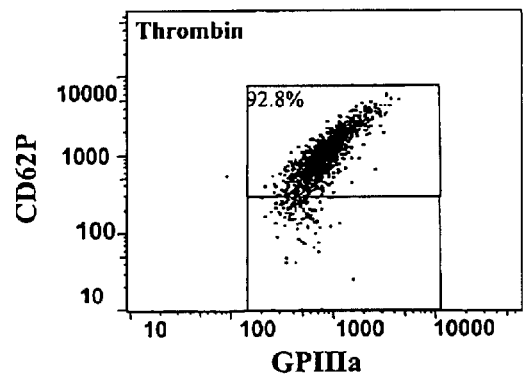
FIG. 5C shows a representative example of the expression of the activation marker CD62P in blood activated with thrombin.
Figure 5D:
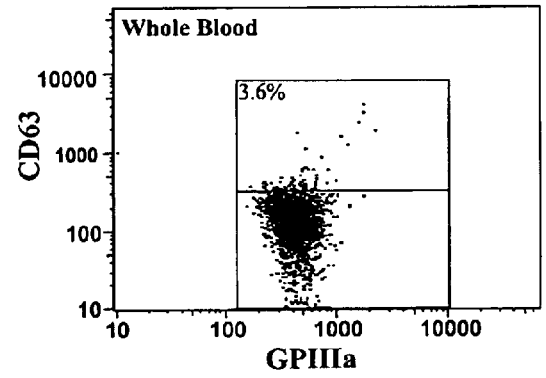
FIG. 5D shows a representative example of the expression of the activation marker CD63 in whole blood.
Figure 5E:
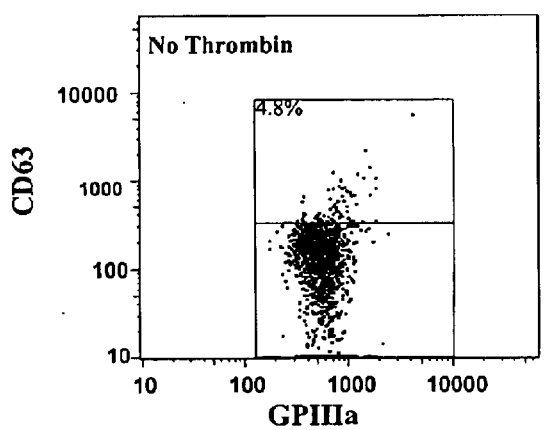
FIG. 5E shows a representative example of the expression of the activation marker CD63in blood activated without thrombin.
Figure 5F:
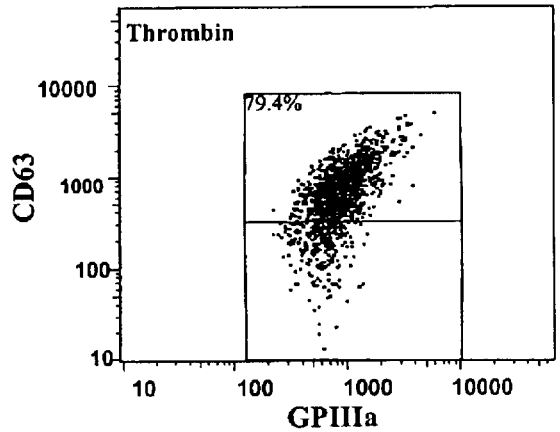
FIG. 5F shows a representative example of the expression of the activation marker CD63in blood activated with thrombin.

The results agree with previous cytometry research using formaldehyde or parafomaldehyde fixed whole blood. Since fixation was not included in the initial processing of the sample, the ability of the platelets to undergo activation was investigated. After a five minute stimulation with thrombin, greater than about 90% of the platelets expressed CD62P (FIGS. 5B and C). Similar results for the thrombin activation and control samples were observed for the 20 samples. See Table III. Similarly, the expression level of CD63 was also greatly increased on the platelets. See FIGS. 5E and F. However, the level of CD63 expression tended to be a bit lower than the level of CD62P expression. In contrast, little increase in the expression of the activation markers was observed in the control (no thrombin) sample. In the absence of thrombin, the sample handling during the stimulation and in the loading of the capillary did not stimulate the platelets. Additional experiments have been done showing that a weaker agonist (relative to thrombin) such as ADP can be used as an activator. After a 30-minute stimulation, greater than 60% of platelets stimulated with ADP express CD62P.

Example 4

Reduction in Unwanted Platelet Background In MLSC

A higher number of background of fluorescent events is observed with blood drawn into EDTA tubes. A comparison between unstained samples of whole blood drawn from the same individual into either a CTAD or EDTA tube was performed. Blood was drawn and handled in an identical fashion. A higher number of background of fluorescence events (1409 vs. 335) is observed with the EDTA sample.

These events reflect the increased platelet activation seen in the EDTA sample. This is demonstrated with CD62P and GPIIIA staining of platelets. Higher levels of CD62P expression are seen on the platelets in the EDTA sample versus the CTAD sample, indicating they are in an activated state. Higher number of background fluorescence events is also observed when fluorescent antibody stains are used. In a further example, whole blood is labeled with Cy5 anti-CD3 which is specific for T cells. There are more total events in the EDTA sample (3544 vs. 2508), which is mainly due to the background events in the EDTA sample compared to the CTAD. Although the CD3 staining is bright, there is some carry over of background events into the CD3 gate. Higher apparent CD3 event counts are observed with the EDTA tube as a result (1333 for EDTA vs. 1175 for CTAD).

The foregoing examples have been presented for the purpose of illustrating the invention and should not be interpreted to restrict the scope or limit the embodiments of the invention.

What is claimed is:

1. A method for measuring the amount of a platelet surface protein in a sample comprising platelets, comprising the steps of:
   (a) contacting the sample with a platelet stabilizing composition comprising an anticoagulant and at least one platelet activation inhibitor;
   (b) incubating the sample obtained in step (a) with a labeled compound having specific affinity for the platelet surface protein; and
   (c) detecting labeled compound bound to platelets by cytometry, whereby the amount of the platelet surface protein is measured, and wherein steps a), b), and c) are performed without fixation of the sample.

2. The method of claim 1, wherein the sample containing platelets comprises whole blood.

3. The method of claim 1 wherein the platelet stabilizing composition is in a collection tube.

4. The method of claim 1, wherein the anticoagulant is citrate.

5. The method of claim 1, wherein at least one platelet activation inhibitor is selected from the group consisting of adenosine, theophyline, dipyridamole and glycyl-L-prolyl-L-arginyl-L-proline.

6. The method of claim 1, wherein the platelet stabilizing composition comprises citrate, adenosine, theophyline and dipyridamole.

7. The method of claim 1, wherein the detection of labeled compounds bound to platelets is by microvolume laser scanning cytometry.

8. The method of claim 1, wherein the detection of labeled compounds bound to platelets is by flow cytometry.

9. The method of claim 1, wherein the detection of labeled compounds bound to platelets is by laser scanning cytometry.

10. The method of claim 1, wherein the labeled compound comprises an antibody against the platelet surface protein.

11. The method of claim 10, wherein the platelet surface protein is selected from the group consisting of p24, GP IIb/IIIb, GPIIIa/IIa, GP Ib/IX/V, GPIIIb/GPIV, GPIba, VLA-2, P-selectin, integrin β1, and lysosomal protein.

12. The method of claim 10, wherein the antibody is a monoclonal antibody selected from the group consisting of anti-CD9, anti-CD41, anti-CD61, anti-CD62P, anti-CD63, anti-CD29, anti-CD42a, anti-CD42b, anti-CD36, anti-CD43, anti-CD100 and anti-CD147.

13. The method of claim 1, wherein said platelet surface protein is found on all platelets.

14. The method of claim 13, wherein the amount of platelet surface protein is used to determine the total number of platelets in the sample.

15. The method of claim 1, wherein said platelet surface protein is only found on activated platelets.

16. The method of claim 15, wherein the amount of platelet surface protein is used to determine the total number of activated platelets in the sample.

17. The method of claim 1, further comprising the step of measuring a cellular or soluble factor of a platelet in said sample.

18. The method of claim 17, wherein the amount of the cellular or soluble factor of a platelet in the sample is measured by enzyme-linked immunosorbent assay.

19. The method of claim 17, wherein the amount of cellular or soluble factor of a platelet in the sample is measured by mass spectrometric analysis.

20. The method of claim 1, wherein the amount of a plurality of platelet surface proteins are measured simultaneously.

* * * * *